United States Patent [19]

Nakagawa

[11] Patent Number: 4,910,014
[45] Date of Patent: Mar. 20, 1990

[54] TEETH CLEANING COMPOSITION WITH SEMICONDUCTIVE TITANIUM OXIDE

[76] Inventor: Yoshinori Nakagawa, 312, Daijishakudo, Taima-cho, Kitakatsuragi-gun, Nara-Ken, Japan

[21] Appl. No.: 223,970

[22] Filed: Jul. 25, 1988

Related U.S. Application Data

[63] Continuation-in-part of Ser. No. 24,331, Jan. 2, 1987, abandoned, which is a continuation-in-part of Ser. No. 625,787, Jun. 28, 1984, abandoned.

[30] Foreign Application Priority Data

Jun. 30, 1983 [JP] Japan ................................ 58-119955

[51] Int. Cl.$^4$ ............................................... A61K 7/16
[52] U.S. Cl. .................................................... 424/49
[58] Field of Search ...................... 424/49, 50; 524/45, 524/55

[56] References Cited

FOREIGN PATENT DOCUMENTS

| | | |
|---|---|---|
| 2239197 | 4/1972 | Fed. Rep. of Germany . |
| 2342363 | 3/1973 | Fed. Rep. of Germany . |
| 2347787 | 9/1973 | Fed. Rep. of Germany . |
| 2348289 | 9/1973 | Fed. Rep. of Germany . |
| 2747852 | 10/1977 | Fed. Rep. of Germany . |

OTHER PUBLICATIONS

Morioka, T., et al., "Antibacterial Action of Powdered Semiconductor on a Serotype g Streptococcus Mutans". (Short Communication). Caries Research, Reprint, vol. 22, No. 4, (pp. 230–231), 1988.
Kawai, Tomoji, et al., (Japanese Language) "Fine Particulate Effect of Semiconductor Photocatalyst". Denki Kagaku, 53, No. 1, (1985).
Kawai, Tomoji, et al. (English Translation of Selected Portions) "Fine Particulate Effect of Semiconductor Photocatalyst".
Saito, Toshiyuki, et al., (Japanese Language) "Antibacterial Effect of Powdered TiO$_2$ with Photocatalytic Reaction on *Streptococcus Mutans* Strain AHT". *Journal of Dental Health*, vol. 36, No. 4, pp. 490–491 (1986).
Saito, Toshiyuki, et al., (English Translation of Selected Portions) "Antibacterial Effect of Powdered TiO$_2$ with Photocatalytic Reaction on *Streptococcus Mutans* Strain AHT".
Saito, Toshiyuki, et al., (Japanese Language) "Bacterial Effect of Powdered TiO$_2$ Suspension with Photocatalytic Reaction on the Growth and the Microscopic Findings of *S. Mutans*". *Journal of Dental Health*, vol. 38, No. 4, pp. 574–575 (1988).
Saito, Toshiyuki, et al. (English Translation of Selected Portions) "Bacterial Effect of Powdered TiO$_2$ Suspension with Photocatalytic Reaction on the Growth and the Microscopic Findings of *S. Mutans*".
Kawai, Tomoji, et al., (Japanese and English Language) "The Structure and the Reactivity of Particulate Semiconductor Photocatalyst". *J. of Am. Chem. Soc.*, 100, No. 2, pp. 277–281, (1978).
Kawai, Tomoji, et al., (English Translation of Selected Portions) "The Structure and the Reactivity of Particulate Semiconductor Photocatalyst".
(Japanese Language) "Kesho-Hin Genryo Kijun, Dai 2-Han Chukai I 1987" Yakujinipposha; (Cosmetic Raw Material Standards, 2nd Edition Explanatory Note, pp. 502–503 (1984).
(English Translation of Selected Portions) "Kesho-Hin Genryo Kijun, Dai 2-Han Chukai I 1987" Yakujinipposha.
Onoda, K., et al., "Photocatalytic Bacterial Effect of Powdered TiO$_2$ on *Streptococcus Mutans*". Denki Kagaku, vol. 56, No. 12, pp. 1108–1109 (1988) Reprints.

(List continued on next page.)

*Primary Examiner*—Morton Foelak
*Assistant Examiner*—Nathan M. Nutter
*Attorney, Agent, or Firm*—Cushman, Darby & Cushman

[57] ABSTRACT

A dentifrice with ordinary components and a powder of n-type semiconductor of titanium dioxide having a purity of at least 99.5% and particle diameter smaller than about 0.04 μm and forming 5 to 10% by weight of said dentifrice, the ordinary components including at least a polishing agent, a foaming agent and a binder.

5 Claims, 4 Drawing Sheets

OTHER PUBLICATIONS

Greene, J. C. and Vermillion, J. R., "The Oral Hygiene Index: A Method for Classifying Oral Hygiene Status", The Journal of the American Dental Assoc., vol. 61, Jul. 1960, No. 1, pp. 172–179.

Rompps-Chemie-Lexikon, 7. Auflage, (1973), pp. 1398–1401.

Landolt–Bornstein, Zahlenwerete und Funktionen, 6. Auflage Bd. IV, 2. Teil, (1965), pp. 700–708.

Ullmanns Encyclopadie der Technischen Chemie, 4. Auflage, Bd. 18, (1979), p. 574.

Ullmanns Encyclopadie der Technischen Chemie, 4. Auflage (1979), Band 18, pp. 582–583.

Volz et al., "Die Photochemischen Abbaureaktionen bei der Bewitterung $TiO_2$-Pigmentierter Bindemittel." *Farbe und Lack*, 82 Jahrg., Nr. 9 (1976), pp. 805–810.

German Office Action, Jun. 25, 1985, p. 34–24–07-4–8–42.

German Office Action, Jan. 23, 1987, P 34–24–07-4–8–42.

German Office Action (English Translation), P 34-2-4–074–8–42, Jan. 23, 1987.

TEETH CLEANING COMPOSITION WITH SEMICONDUCTIVE TITANIUM OXIDE

This application is a continuation-in-part of application Ser. No. 07/024,331, filed Jan. 2, 1987, now abandoned, which was a continuation-in-part of application Ser. No. 06/625,787, filed June 28, 1984, now abandoned.

BACKGROUND OF THE INVENTION

The invention relates to certain kinds of cosmetics and quasi-pharmaceuticals, and more particularly to a teeth cleaning composition (hereinafter referred to as "dentifice") which is daily used to remove the stain, dental plaque from teeth and also to remove the food dregs from the gaps between teeth in order to clean up the oral cavity and to maintain the cleanliness thereof. The dentifrice includes a tooth powder and a tooth paste kneaded fully or semi-kneaded.

The dentifrices which have been widely used are composed in general of polishing or cleaning agents, foaming agents, binders and other components. These ordinary components are merely effective to remove the stains from teeth by utilizing a physical grinding effect of the polishing agent and a toothbrush. Foams produced thereby within the oral cavity also plays a considerable role.

The known dentifrices are however disadvantageous in that the surface enamel layers of teeth are injured if the grinding effect of said polishing agent and toothbrush is intensified too much. Consequently, the known dentifrices have only a limited effect in cleaning teeth and are almost impossible to remove the dental plaque from teeth.

SUMMARY OF THE INVENTION

In view of the above, the invention provides a dentifrice which gives rise to a photocatalytic reaction caused by a semiconductive material contained in said dentifrice and the light energy incident on said material, the dentifrice thereby having a cleaning effect much higher than that of the known dentifrices which contribute only to the physical grinding of teeth.

An object of the invention is therefore to provide a dentifrice comprising a polishing agent, foaming agent, binders and the other ordinary components, as well as a powder of n-type semiconductor, the powder having particle diameter smaller than about 0.04 μm. This powder causes a photocatalytic reaction as described below in detail.

Preferable n-type semiconductors are titanium dioxide of high purity, and ferric oxide. The best n-type semiconductor in the invention is highly pure titanium dioxide which is contained in a detifrice at about 5 to 10% by weight and which has particle diameter smaller than about 0.04 μm (average particle diameter being about 0.014 μm). A TiO$_2$ content above 10% by weight causes a lower efficiency of utilization of the light energy. A content below 5% by weight is also not preferred because TiO$_2$ cannot produce a sufficient effect as mentioned below in detail. Thus, the most desirable TiO$_2$ content is from about 5% to about 10% by weight. Further, if the particle diameter exceeds about 0.04 μm, there occurs less active photocatalytic reaction.

TiO in the invention is to be of as high a purity as possible and preferablly higher than 99.5% and more preferably above 99.98% in order to be semiconductive.

An example of a method to produce such a pure TiO$_2$ will be described hereinafter.

According to the invention, the powder of n-type semiconductor is scattered around the teeth with water or saliva interposed between particles of the powder, when the dentifrice is used. The light, which may be the natural light, will shine upon the semiconductor powder to produce excited photoelectrons therein. Accordingly, a number of "holes" appear in each particle of the powder due to the electric potential difference in space charge layer, the space charge layer being inherent in semiconductive materials. The holes tend to obtain electrons from water, thus producing chemically active OH-radicals.

Details of the above mechanism will be illustrated as follows, when a powder of titanium dioxide (TiO$_2$) is used as the semiconductive powder.

The holes are generated in the space charge layer of TiO$_2$ particles according to the first step (1):

$$TiO_2 + h \rightarrow P^+ + e^- \qquad (1)$$

where P$^+$ is each of the holes, and e$^-$ is each of the excited electrons.

The holes on the TiO$_2$ particles will then take the electrons away from the water molecules contained in saliva. This process is represented by the following formula and referred to as the second step (2):

$$H_2O + P^+ \rightarrow .OH + H^+ \qquad (2)$$

where .OH is each of the OH-radicals.

This second step (2) is schematically shown in the accompanying FIG. 1 of the drawings.

Though this will be more particularly described later, the OH-radicals act on and decompose the organic substances such as the tartar, in such a manner as outlined hereinafter. The decomposition of the dental plaque results in a decrease in amount of acids produced by said dental plaque, thus preventing the decalcification of teeth which is caused by lower pH-value of teeth. Also, the OH-radicals have bactericidal effect against *S. mutants* (*Streptococcus mutans*) or the like.

The inventor assumes that the above mentioned decomposition would happen as follows. Namely, the main component of the dental plaque of teeth is dextran which is a polycondensate of glucose molecules and is attacked by the active OH-radicals so as to be decomposed according to the following formula (3):

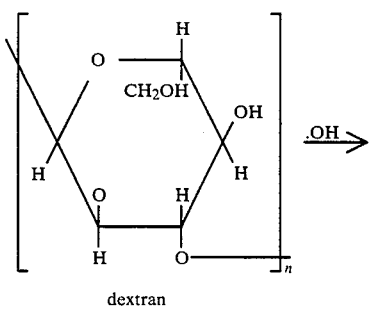

dextran

-continued

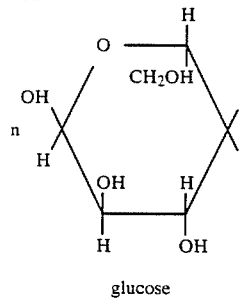

glucose where n is an integral number.

The inventor also assumes that the active OH-radicals are very effective to act on and decompose some organic acids such as lactic acid which causes the decalcification of teeth. The decomposition of lactic acid may take place in such a manner as shown in the following formula (4):

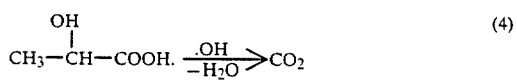

A simulation test result is now described referring to FIG. 2 in which decomposition of lactic acid is shown in case of using the semiconductive $TiO_2$ powder in comparison with a case of ordinary $TiO_2$.

An aqueous solution of lactic acid of 90 ppm was mixed with 2 wt.% of dentifrices, one of which contained the semiconductive $TiO_2$, the other cotaining the ordinary $TiO_2$. Remaining quantities of lactic acid (shown on axis of ordinates) after irradiation by mercury lamp light for 6 hours varied with regard to $TiO_2$ content in the dentifrices (shown on axis of abscissas).

The ordinary $TiO_2$ was of a purity of about 98% whereas the semiconductive one was of 99.98% purity.

As shown in FIG. 2, the dentifrice comprising the ordinary $TiO_2$ has proved almost inefficient for lactic acid decomposition even at a high $TiO_2$ content such as 10 wt.%. Contrary to this, the other dentifrice comprising the $TiO_2$ of 99.98% purity decomposed lactic acid almost perfectly at a $TiO_2$ content of 5 wt.%.

Next, a result of a more practical test will be explained below. Two kinds of paste were used, one of which consisted of: 3 wt. % CMC-sodium (carboxymethyl cellulose-sodium), 3 wt. % of carrageenane, 5 wt.% of glycerol, 0.3 wt. % of 99.98 purity semiconductive $TiO_2$, and 88.7 wt.% water. The other paste did not comprise the TiO with the other components unchanged and contained 89 wt. % water.

Thickness of dental plaque on teeth was measured before and after irradiation of light for 5 minutes onto the teeth to which the pastes had been applied. The measurement was effected by dyeing the dental plaque with a dyestuff solution (comprising Erythrosine, and Brilliant blue FCF, each at 3 wt.%), and by subsequently conducting a colorimetric method to the dyed dental plaque. According to a proportional relationship which had been established between the density of the color and a thickness of the dental plaque, it was proved that an average thickness of dental plaque on 38 (thirty eight) teeth had changed from 37.5 μm to 15.0 μm by the irradiation of light in case of the paste comprising the semiconductive $TiO_2$. Thus, the dental plaque was diminished by 22.5 μm. However, in case of the other paste containing no $TiO_2$, the dental plaque thickness had decreased from 40.5 μm to 21.0 μm, thus giving a decrease by 19.5 μm.

The difference between the decreases of dental plaque thickness, namely, 22.5−19.5=3 μm, is regarded to be an effect of the semiconductive $TiO_2$ of 99.98% purity. The blank value 19.5 μm would be a disturbance factor caused by the dyeing and washing operation per se.

Next, experiments were conducted for checking the germicidal effect of the dentifrice of the invention against S. mutans or the like which are considered to contribute to development of tooth decay.

First, as $TiO_2$ content of the dentifrice composition shown in Table 1, the experiments were conducted for comparison using three types of dentifrice compositions A, B and C: the composition A containing $TiO_2$ having average particle diameter of 0.014 μm, with a particular diameter being smaller than 0.04 μm composition B containing $TiO_2$ of average particle diameter of 0.3 μm without surface treatment, composition C containing $TiO_2$ of average particle diameter of 0.4 μm having its surface treated e.g. with inorganic oxide often used in dentifrices and cosmetics. In the composition A, the purity of $TiO_2$ was 99.5%. The results of the experiments are shown in FIG. 3; whereas FIG. 4 shows the results of experiments where no light was applied to the compositions.

Incidentally, functions of the dentifrice compositions will be particularly describe later.

The S. mutants used in the above experiments had been anaerobicly cultured in BHI (Brain Heart Infusion) broth and then well suspended in physiological salt solution. The light source was a 20 W fluorescent lamp capable of emitting a good amount of near ultraviolet rays. This light source was set at 5 cm from the samples and the liquid temperature was set to be 37° C.

Further, the compositions were mechanically stirred in both experiments with and without the light irradiation. And, the number of living bacteria per 0.5 ml was checked chronologically.

The results in FIGS. 3 and 4 clearly show that the photocatalytic reaction is most active in the case of super-fine particle having particle diameter smaller than 0.04 μm.

TABLE 1

| components | wt. % |
|---|---|
| precipitated calcium carbonate | 30.0 |
| silicic anhydride | 1.1 |
| $TiO_2$ | 5.0 |
| glycerine | 26.0 |
| CMC—Na | 1.3 |
| sodium lauryl sulfate | 1.5 |
| perfume | 1.0 |
| tween 80 | 0.2 |
| butyl parahydroxybenzoate | 0.02 |
| dipotassium glycyrrhizinate | 0.2 |
| saccharine-sodium | 0.1 |
| water | 33.58 |
| total | 100.00 |

TABLE 2

| components | D compo. % | E compo. % |
|---|---|---|
| heavy calcium carbonate | 25.0 | 25.0 |
| silicic anhydride | 3.0 | 3.0 |
| semiconductor $TiO_2$ | 5.0 | — |
| polyethylene glycol 400 | 20.0 | 20.0 |
| carrageenane | 1.0 | 1.0 |
| sodium lauryl sulfate | 1.0 | 1.0 |

TABLE 2-continued

| components | D compo. % | E compo. % |
| --- | --- | --- |
| butyl parahydroxybenzoate | 0.02 | 0.02 |
| perfume | 0.9 | 0.9 |
| tween 80 | 0.2 | 0.2 |
| saccharine-sodium | 0.2 | 0.2 |
| dipotassium glycrrhizinate | 0.2 | 0.2 |
| water | 43.48 | 43.48 |
| total | 100.00 | 95.00 |

*'comp' is short for composition

By daily using the dentifrice containing the semiconductor $TiO_2$, the contribution of the photocatalytic reaction to oral hygiene was ascertained. Incidentally, the semiconductor $TiO_2$ used here has the average particle diameter of 0.014 μm.

METHOD OF EXPERIMENTS

The dentifrices compositions D and E shown in Table 3 were used respectively for one month by subject persons consisting of 11 (eleven) female adults, and the subject persons were inspected once a week. The subjects were not provided, prior to the experiments, with any tooth-brushing instructions or dental calculus removal treatment and they were advised to brush their teeth as usual.

As for the testing method, both the OHI-S (Oral Hygiene Index Simplified) and the Cariostat (carious growth testing) methods were used.

RESULTS OF EXPERIMENTS

Of the OHI-S evaluation values, the DI-S (Debris Index Simplified) values were singled out and tabulated in Tables 3 through 5.

It is to be noted that the numerical values in these tables comprise % (percentage) representations of debris with the maximum value in the DI-S being 100.

Table 3 shows values obtained by the statistically-processed sum values for 4 weeks of nine upper-jaw teeth faces and twelve lower-jaw teeth faces.

Table 4 shows values obtained by the statistically-processed sum values for 4 weeks of three upper-jaw teeth faces and seven lower-jaw teeth faces.

Table 5 shows values obtained by the statistically-processed sum values for 4 weeks of fifteen upper-jaw teeth faces and twelve lower-jaw teeth faces.

Next, the results by the carious growth testing method (carious growth at 48 hours later) are shown in Table 6.

Table 6 shows the results by the method of 4-weeks sum (40 teeth) of 10 upper and lower jaw teeth.

TABLE 3

| | DI-S of front teeth | |
| --- | --- | --- |
| portion | D compo. (with semicon.) | E compo. (without semicon.) |
| upper jaw | 23.1 | 30.6 |
| lower jaw | 27.8 | 30.6 |

*'semicon.' is short for semiconductor

TABLE 4

| | DI-S of premolars | |
| --- | --- | --- |
| portion | D compo. (with semicon.) | E compo. (without semicon.) |
| upper jaw | 22.2 | 30.6 |
| lower jaw | 51.2 | 60.7 |

TABLE 5

| | DI-S of molars | |
| --- | --- | --- |
| portion | D compo. (with semicon.) | E compo. (without semicon.) |
| upper jaw | 27.8 | 42.8 |
| lower jaw | 55.6 | 61.1 |

TABLE 6

| | carious growth testing values of molars | |
| --- | --- | --- |
| evaluation | D compo. (with semicon.) | E compo. (without semicon.) |
| + | 5 | 1 |
| + | 9 | 5 |
| 1.5+ | 22 | 14 |
| 2+ | 4 | 20 |

From the results shown in Tables 3 through 5, it may be seen that the daily use of the dentifrice containing the semiconductor $TiO_2$ contributes to decrease of dental plaque adhesion at all the oral portions.

From the results (of Cariostat) shown in Table 6, it may be seen that the carious growth becomes less active by the daily use of the dentifrice containing the semiconductor $TiO_2$.

It will now be understood that the dentifrice of the invention serves effectively to protect teeth from the decaying thereof and pyorrhea and also to accelerate the cleaning of teeth. The surface enamel layers of teeth are not injured because the dentifrice of the invention exclude a necessity of the excessively strong physical power which would otherwith be exerted to teeth in use of the known dentifrices.

The most important advantage of the invention resides in a fact that the powder of n-type semiconductor is spread over the entire space of the oral cavity and comes into contact with the teeth surface inclusive of the backsides thereof whereby said semiconductor powder gives an excellent effect in preventing the teeth from being decayed and also from suffering from pyorrhea. This effect is superior to that which have been achieved by using a toothbrush having a n-type semiconductor piece attached thereto so as to utilize a photo-electrochemical function of said piece.

DETAILED DESCRIPTION OF THE PREFERRED EMBODIMENTS

Figure 1:
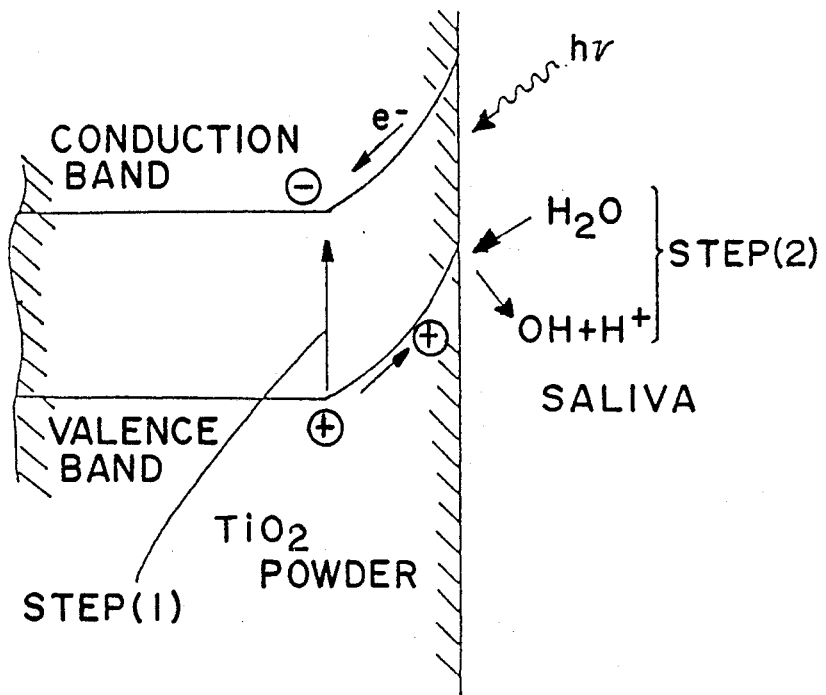
FIG. 1 schematically illustrates a mechanism of generating of OH-radicals which takes place when beams of light are irradiated on $TiO_2$ powder in saliva.
Figure 2:
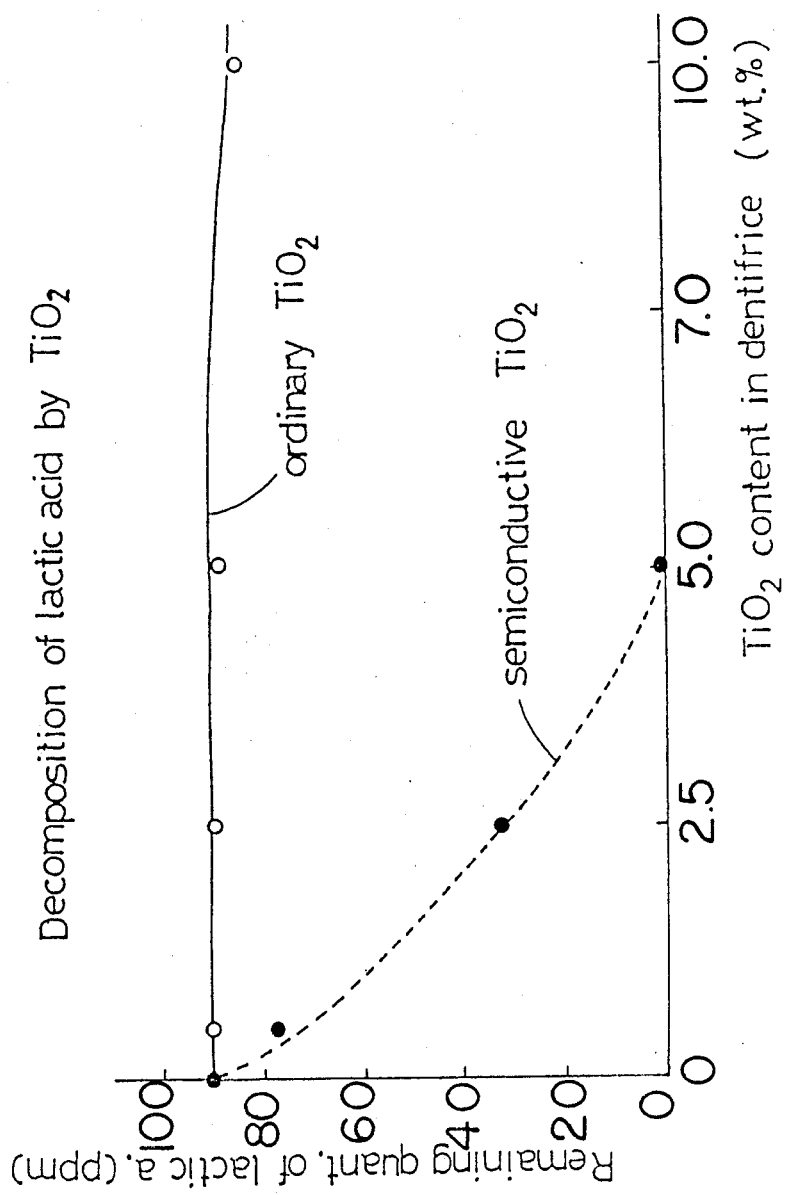
FIG. 2 is a graph showing decomposition of lactic acid in relation with $TiO_2$ contents in dentifrices.
Figure 3:
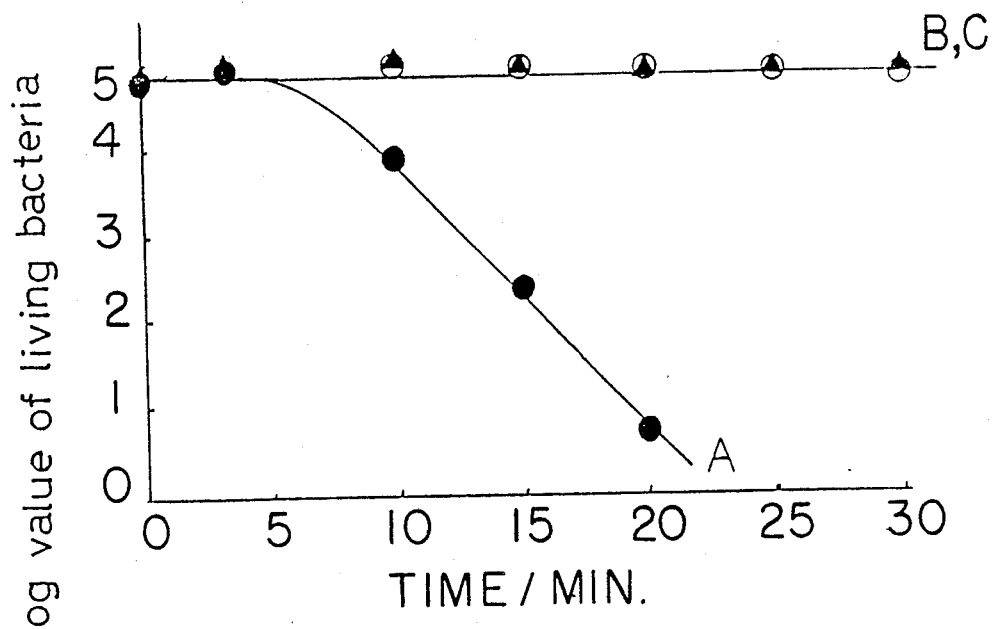
FIG. 3 is a graph showing comparison between bactericidal effects under light irradiation of the dentifrice containing the $TiO_2$ powder of the present invention and of a dentifrice containing another type of $TiO_2$ powder.
Figure 4:
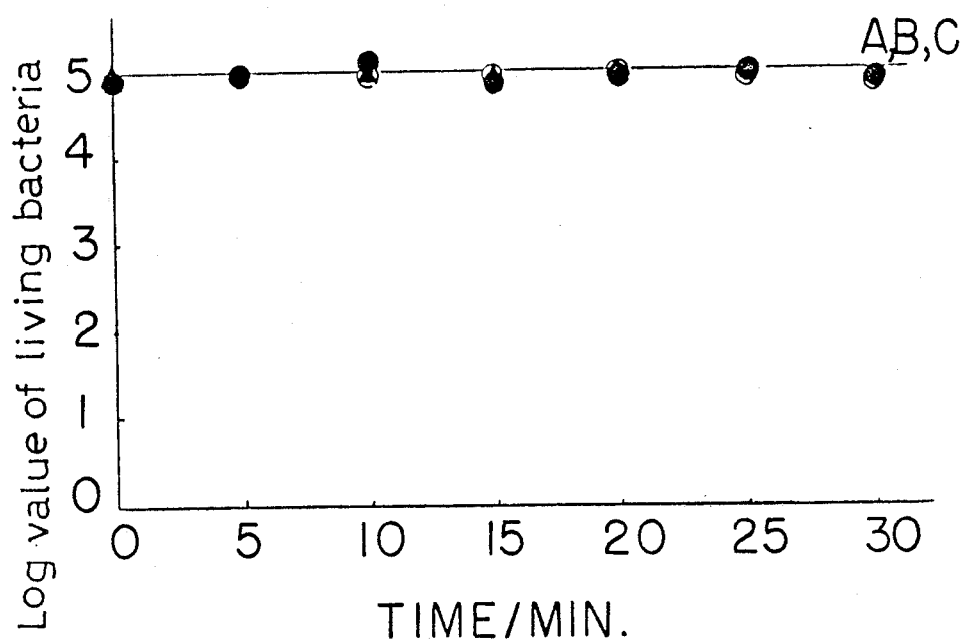
FIG. 4 is a graph showing bactericidal effects of the same dentifrice components without light irradiation.

Some embodiments are now described below.

In the first embodiment, a dentifrice is the so-called tooth paste and comprises (as shown in Table 7):

1. calcium hydrogen phosphate as the polishing or cleaning agent;
2. sorbitol and propylene glycol as a humectant;

3. sodium lauryl sulfate as the foaming agent;
4. sodium carboxymethyl cellulose as the binder;
5. the other components such as a preservative, water, a perfume and sweetening agent;
6. chlorohexidine hydrochloride as sterilizer; and
7. a powder of titanium dioxide ($TiO_2$) as the powder of the n-type semiconductor.

The above components are contained in the tooth paste in the ratio (% by weight) as given in the Table 1. The $TiO_2$ powder is adapted to generate a photoelectromotive force in an appropriate solution and to fuction as a photocatalyst when irradiated with the light entering the oral cavity during a tooth brushing operation. In particular, said $TiO_2$ powder is prepared by purifying, calcinating and thereafter pulverizing an amount of raw ilmenae. In more detail, the $TiO_2$ of purity at 99.5% or higher is manufactured, for instance, in the following manner.

The starting material is ordinary marketed $TiO_2$ of 98% purity. Carbon powder is mixed with the ordinary TiO to form small balls. These balls are then sintered and thereafter heated to 800° C. in chlorine gas so as to change into titanium tetrachloride ($TiCl_4$). This $TiCl_4$ is subsequently calcinated at 1,000° to 1,500° C. to be oxidized, or alternatively, is hydrolyzed, washed with water, sintered and finally pulverized. The thus obtained $TiO_2$ include only a very little amount of impurities at 0.5% by weight or less.

TABLE 7

| Contents of Components | |
|---|---|
| components | wt. % |
| calcium hydrogen phosphate | 45 |
| silicic anhydride | 2 |
| sorbite, propylene glycol | 10 |
| sodium lauryl sulfate | 2 |
| sodium carboxymethyl cellulose | 1 |
| perfume, saccharine-sodium | 1 |
| water | 32.9 |
| chlorohexidine hydrochloride | 4 |
| titanium dioxide ($TiO_2$) | 5 |
| parahydroxybenzoate | 0.1 |

The other embodiments are:
second embodiment in which the $TiO_2$ powder is contained at a wt % different from that shown in Table 7;
third embodiment in which the components other than $TiO_2$ powder are contained at wt % different from those listed in Table 7;
fourth embodiment in which the $TiO_2$ powder in the first embodiment is substituted by any other powder of n-type semiconductor such as $Fe_2O_3$, which are harmless to human body; and
fifth embodiment in which the kinds and contents of components as well as the content of $TiO_2$ powder are different from those listed in Table 7.

An embodiment of the components according to the fifth embodiment as given in Table 8.

TABLE 8

| (fifth embodiment) | | |
|---|---|---|
| components | functions | wt. % |
| calcium carbonate | A | 40 |
| heavy calcium carbonate | A | 40 |
| glycerine | B | 1.65 |
| sodium lauryl sulfate | C | 2 |
| ethyl parahydroxybenzoate | D | 0.1 |
| chlorhexidine gluconate | E | 0.1 |
| titanium dioxide (TiO) | F | 10 |
| peppermint | G | 1.25 |
| saccharine sodium | H | 0.1 |
| water | | 4.8 |

Note:
The reference A indicates the polishing agents, B indicates the humectant, C indicates the foaming agent, semiconductor, G indicates the perfume, and H indicates the sweetner

What is claimed is:

1. A dentifrice with semiconductive titanium oxide comprising:
   a polishing agent;
   a foaming agent;
   a binder;
   a powder of n-type semiconductor of titanium dioxide powder forming 5 to 10% by weight of said dentifrice and to produce excited photoelectrons in response to incident light and chemically active OH-radicals wherein said titanium dioxide powder has particle diameter smaller than about 0.04 μm.

2. A dentifrice as claimed in claim 1, wherein the dentifrice is a tooth paste.

3. A dentifrice as claimed in claim 1, wherein the dentifrice is a semi-kneaded tooth paste.

4. A dentifrice as claimed in claim 1, wherein the dentifrice is a tooth powder.

5. A dentifrice with semiconductive titanium oxide comprising:
   a polishing agent;
   a foaming agent;
   a binder; and
   a powder of n-type semiconductor of a purity at least 99.5% and forming 5 to 10% by weight of said dentifrice.

* * * * *